US009469833B2

(12) United States Patent
Nakayama (10) Patent No.: US 9,469,833 B2
(45) Date of Patent: Oct. 18, 2016

(54) TRANSPLANTATION GUIDE AND TRANSPLANTATION DEVICE

(75) Inventor: Koichi Nakayama, Saga (JP)

(73) Assignee: CYFUSE BIOMEDICAL K. K., Tokyo (JP)

( * ) Notice: Subject to any disclaimer, the term of this patent is extended or adjusted under 35 U.S.C. 154(b) by 0 days.

(21) Appl. No.: 13/983,494

(22) PCT Filed: Feb. 3, 2012

(86) PCT No.: PCT/JP2012/052475
§ 371 (c)(1),
(2), (4) Date: Sep. 6, 2013

(87) PCT Pub. No.: WO2012/105680
PCT Pub. Date: Aug. 9, 2012

(65) Prior Publication Data
US 2013/0337553 A1 Dec. 19, 2013

(30) Foreign Application Priority Data

Feb. 4, 2011 (JP) .................. 2011-023348

(51) Int. Cl.
| C12N 5/00 | (2006.01) |
| C12N 5/02 | (2006.01) |
| C12M 1/26 | (2006.01) |
| C12M 1/12 | (2006.01) |
| A61B 17/00 | (2006.01) |

(52) U.S. Cl.
CPC .............. *C12M 33/00* (2013.01); *C12M 23/06* (2013.01); *C12M 25/02* (2013.01); *C12M 33/04* (2013.01); *A61B 2017/00004* (2013.01); *A61B 2017/00907* (2013.01); *A61B 2017/00969* (2013.01)

(58) Field of Classification Search
None
See application file for complete search history.

(56) References Cited

U.S. PATENT DOCUMENTS

| 6,017,348 A | 1/2000 | Hart et al. |
| 7,166,133 B2 | 1/2007 | Evans et al. |
| 2001/0014473 A1 | 8/2001 | Rieser et al. |
| 2007/0020754 A1 | 1/2007 | Yuge et al. |
| 2011/0106005 A1 | 5/2011 | Iwamoto et al. |

FOREIGN PATENT DOCUMENTS

| EP | 1 541 182 A1 | 6/2005 |
| JP | 2000-513214 A | 10/2000 |
| JP | 2002-534210 A | 10/2002 |
| JP | 2004-216119 A | 8/2004 |

(Continued)

OTHER PUBLICATIONS

Extended European Search Report dated Nov. 20, 2014, for European Application No. 12741664.2.

(Continued)

*Primary Examiner* — Thomas J Visone
(74) *Attorney, Agent, or Firm* — Birch, Stewart, Kolasch & Birch, LLP (57) ABSTRACT

The present invention provides a transplantation guide which is formed into a bottomed cylinder having a base material that allows communication of a culture fluid, wherein:
  a cell mass supplied from the open end side is placed on the base material, and
  the guide is used as a mold for forming a three-dimensional cell construct by culturing the cell mass placed on the base material by immersing the base material side in an excessive amount of a culture fluid.

6 Claims, 5 Drawing Sheets

(56) References Cited

FOREIGN PATENT DOCUMENTS

| | | | | |
|---|---|---|---|---|
| JP | 2004-357694 | * | 12/2004 | .............. C12N 5/06 |
| JP | 2004-357694 A | | 12/2004 | |
| JP | 2006-513013 A | | 4/2006 | |
| JP | 2006-527009 A | | 11/2006 | |
| JP | 2007-502127 A | | 2/2007 | |
| JP | 2010-241756 A | | 10/2010 | |
| WO | WO 98/34569 A1 | | 8/1998 | |
| WO | WO 00/41648 A1 | | 7/2000 | |
| WO | WO 2004/078954 A1 | | 9/2004 | |
| WO | WO 2004/104183 A2 | | 12/2004 | |
| WO | WO 2005/037984 A1 | | 4/2005 | |
| WO | WO 2009/081503 A1 | | 7/2009 | |
| WO | WO 2010/117043 A1 | | 10/2010 | |

OTHER PUBLICATIONS

Shimoto et al., "Building of HD MACs Using Cell Processing Robot for Cartilage Regeneration," Journal of Robotics and Mechatronics, vol. 24, No. 2, 2012, pp. 347-353.

* cited by examiner

TRANSPLANTATION GUIDE AND TRANSPLANTATION DEVICE

TECHNICAL FIELD

The present invention relates to a transplantation guide for transplanting a three-dimensional cell construct into an affected area and a transplantation device for transplanting a three-dimensional cell construct into an affected area by using said transplantation guide.

BACKGROUND ART

Recently, studies of regenerative medicine are making progress. For example, in regenerative medicine, artificially cultured cells are used instead of the damaged cells in an affected area for regenerative treatment of the affected area. As a method for culturing such cells, for example, two-dimensional culture is conventionally well known, in which cells are cultured on a Schale, or a petri dish, and the cells formed by the two-dimensional culture are peeled off from the Schale, or the petri dish, after a specific treatment, to be used in an affected area. For example, Patent Document 1 describes a method for generating a chondroid tissue used for treating damaged cartilage in a joint, according to which the method for generating a chondroid tissue is improved.

Furthermore, in order to enhance the therapeutic effect, techniques for three-dimensionally culturing cells that are used for regenerative medicine have been developed. Cultivation methods that use a support as a scaffold upon cultivation have already been devised for a three-dimensional cell cultivation, and, for example, Patent Documents 2 and 3 describe improved supports.

On the other hand, techniques for three-dimensionally culturing cells without using a scaffold have also been developed. For example, Patent Document 4 describes a method for three-dimensionally culturing cells without using a scaffold but by immersing the cells in an excessive amount of a culture fluid.

In a case where a three-dimensional construct resulting from three-dimensional cell cultivation is to be transplanted, a transplantation device intended for handling a three-dimensional cell construct (see Patent Document 5) can be used. This may reduce risks such as bacterial contamination, and thus this technique has been receiving attention.

For transplantation of a three-dimensional construct, in order to adapt a three-dimensional construct, which is to be supplied to a hollow-like-shaped recipient site, to a living body as much as possible, a three-dimensional construct with a size close to the size of the recipient site needs to be inserted into the affected area. When a three-dimensional construct with a size close to the size of the recipient site is to be inserted into the recipient site, however, a clearance between the three-dimensional construct and the recipient site becomes small, which renders insertion of the three-dimensional construct into the recipient site difficult.

On the other hand, if the clearance is made larger, the size of the three-dimensional construct becomes smaller with respect to the size of the recipient site and may possibly fail to bring about a desirable therapeutic effect.

Therefore, in order to deal with a case where a clearance is as small as, for example, 0.2 mm or less between the three-dimensional construct and the recipient site, delivery of the three-dimensional construct to the recipient site by using a thinly-formed cylindrical guide was considered. Such a thin guide, however, is very fine and sensitive, and thus has sometimes been difficult to transfer the three-dimensional construct into such a fine guide.

PRIOR ART DOCUMENTS

Patent Documents

[Patent Document 1] Japanese Unexamined Patent Application Publication (Translation of PCT Application) No. 2007-502127

[Patent Document 2] Japanese Unexamined Patent Application Publication No. 2004-216119

[Patent Document 3] Japanese Unexamined Patent Application Publication (Translation of PCT Application) No. 2006-513013

[Patent Document 4] Japanese Unexamined Patent Application Publication No. 2004-357694

[Patent Document 5] International Patent Publication No. WO2009/081503 (pamphlet)

SUMMARY OF INVENTION

Problem To Be Solved By the Invention

Regarding the above-described circumstances, the present invention has an objective of providing a transplantation guide and a transplantation device for supplying a cell mass to an affected area by handling the cell mass without requiring a user to directly touch the cell mass.

Means For Solving the Problem

In order to accomplish the above-described objective, a transplantation guide of the present invention is characterized in that it is formed into a bottomed cylinder having a base material that allows communication of a culture fluid, wherein a cell mass supplied from the open end side is placed on the base material, and the guide is used as a mold for forming a three-dimensional cell construct by culturing the cell mass placed on the base material by immersing the base material side in an excessive amount of a culture fluid.

The thickness of the cylinder is preferably as thin as possible. For example, it is preferably 0.05-0.3 mm.

In addition, a transplantation device of the present invention is characterized by holding the above-described transplantation guide wherein the transplantation guide is withdrawn from a recipient site while making the three-dimensional cell construct placed on the base material to be retained at the recipient site of a patient.

EFFECT OF THE INVENTION

Since the transplantation guide of the present invention serves as a guide for delivering a cell mass to an affected area while it also serves as a mold for the cell mass, the number of user's tasks for cultivation and transplantation can be reduced, thereby enhancing convenience.

In addition, since the transplantation device of the present invention is capable of grasping the open end of the transplantation guide holding the cell mass inside and capable of making the three-dimensional cell construct to be retained at the recipient site without the three-dimensional cell construct touching the hand of the user, bacterial and microbial contamination of the cell mass can be reduced.

EMBODIMENTS FOR CARRYING OUT THE INVENTION

A transplantation guide of the present invention is characterized by being formed into a bottomed cylinder having a base material that allows communication of a culture fluid, wherein a cell mass supplied from the open end side is placed on the base material, and the guide is used as a mold for forming a three-dimensional cell construct by culturing the cell mass placed on the base material by immersing the base material side in an excessive amount of a culture fluid.

Since one end of this transplantation guide is held by a user and the other end is inserted into a recipient site of a patient, the thinner the cylinder (thickness of the lateral wall of the cylinder) is, the larger three-dimensional cell construct supplied to the recipient site can be. Thus, the thickness of the cylinder is preferably as thin as possible.

Figure 1:
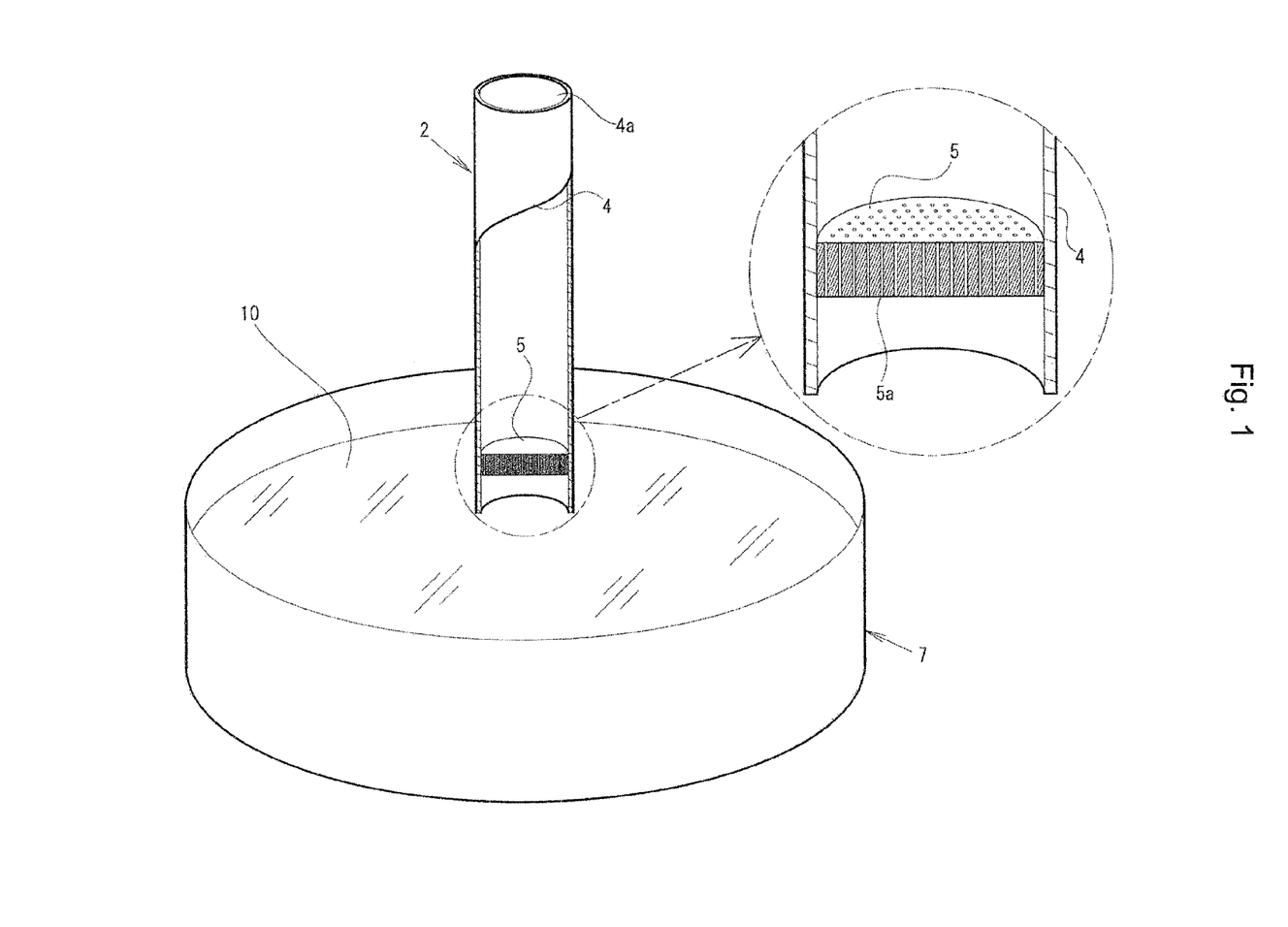
FIG. 1 A view for illustrating cultivation of cells by immersing a base material side of a transplantation guide of the present invention in a vessel accommodating an excessive amount of a culture fluid.

FIG. 1 is a view for illustrating cultivation of culture cells by immersing a base material side of a transplantation guide of the present invention in a vessel accommodating an excessive amount of a culture fluid. As shown in FIG. 1, a transplantation guide 2 of the present invention is formed into a bottomed cylinder, and comprises a cylindrical body 4 and a disk-like base material 5 integrated in this cylindrical body 4. The shape of the cylinder is not particularly limited and it may take a shape of a circular cylinder as shown in FIG. 1 or a rectangular cylinder, and any optimal shape may be selected according to the shape of the affected area since the cylinder itself is used as a mold.

One end of the cylindrical body 4 is open while the other end is provided with the base material 5, by which the transplantation guide 2 is formed into a vessel that can reserve an object inside.

A cellular culture fluid containing culture masses such as spheroids is poured from the opening 4a of the transplantation guide 2, and the cell masses poured from the opening 4a are held within the cylinder due to the base material 5.

The base material 5 has micropores 5a that allow communication of the culture fluid. These micropores 5a allows the culture fluid poured into the cylindrical body 4 to communicate with the external area and at the same time allow the culture fluid from the external area to communicate with the interior area of the cylindrical body 4.

When the base material 5 side of the transplantation guide 2 is immersed in the vessel 7 accommodating the excessive amount of the culture fluid 10, the excessive amount of the culture fluid 10 filling the vessel 7 communicates with the interior area of the transplantation guide 2 via the base material 5 while the culture fluid in the transplantation guide 2 communicates with the vessel 7. Owing to such communication of the culture fluids, the cultured cells in the transplantation guide 2 can be cultured to a three-dimensional cell mass, and the cultured cell mass, in turn, can be formed, for example, into a column shape following the shape of the transplantation guide 2. As described above, the transplantation guide 2 can serve as a mold (template) for forming a three-dimensional construct upon cultivation of the spheroids or the like.

The excessive amount of the culture fluid accommodated in the vessel 7 is not particularly limited as long it allows the cells to proliferate/differentiate. For example, when a three-dimensional construct with a diameter of 4 mm and a thickness of 5 mm is to be cultured in the transplantation guide 2, the amount of the culture fluid required in the transplantation guide 2, for example, is 1-2 ml while the excessive amount of the fluid filling the vessel 7 is about 5-10 times the amount of the culture fluid in the transplantation guide 2, for example, preferably 10-20 ml.

Examples of a material of the cylindrical body 4 constituting the transplantation guide 2 include rust-resistant metal materials such as stainless, and polymeric materials that have good weather resistance, chemical resistance and corrosion resistance. In particular, the cylindrical body 4 of the transplantation guide 2 is preferably formed with a polymeric material in terms that the three-dimensional construct formed inside can be observed, that it is flexible and elastic to some extent and that it can be made transparent/semi-transparent.

Typical examples of such a polymer include fluoropolymers, examples being polytetrafluoroethylene (PTFE), polychlorotrifluoroethylene, polyvinylidene difluoride (PVDF), polyvinyl fluoride (PVF) and fluoroplastic copolymers such as polytetrafluoroethylene-hexafluoropropylene copolymer (FEP), among which polytetrafluoroethylene is particularly preferable.

The cylindrical body 4 is preferably formed to have a uniform thickness that is within a range of, for example, 0.05 mm-0.3 mm, and particularly preferably a thickness that is within a range of 0.1 mm-0.2 mm.

The base material 5 is porous with a plurality of micropores 5a. The size of these micropores 5a needs to be smaller than the size of a culture mass and large enough to allow the culture fluid to pass therethrough. As one example, the pore diameter of the micropores 5a is 10-500 μm so that a three-dimensional construct does not pass through the base material 5 and only the culture fluid can go in and out of the base material 5.

Preferably, the base material 5 is formed with a biodegradable material. An example of such a biodegradable material includes synthetic calcium phosphate ceramics, where examples of such calcium phosphate include alpha-tricalcium phosphate, beta-tricalcium phosphate and hydroxyapatite. Among them, alpha-tricalcium phosphate or beta-tricalcium phosphate is particularly preferable.

By forming the base material 5 with the above-mentioned material that degrades in a living body, this base material 5 can be supplied together with the three-dimensional construct to an affected area, thereby enhancing convenience.

Cells that can be targeted for cultivation (cells making a cell mass) are, for example, undifferentiated or differentiated cells of a stem cell (ES cell, umbilical blood-derived cell, undifferentiated mesenchymal cell, etc.), a somatic cell, a tumor cell or the like.

A fibroblast cell, a stem cell, a vascular endothelial cell, an epidermal cell, an epithelial cell, an osteoblast, a chondrocytic cell and an adipose cell can easily be induced to differentiate from an undifferentiated mesenchymal stem cell. Cells such as articular chondrocytic cells and osteocytes can also be used.

Thus, the present invention can be applied to an articular cartilage and a bone as well as an adipose cell such as breast, a ligament and the like, while using a mesodermal tissue as a core.

Cells are broadly grouped into anchorage-independent cells and anchorage-dependent cells, where the blood cells and the immune system cells belong to the former while the epidermal cells and the osteocytes belong to the latter. The epidermal cells and the osteocytes will die in floating conditions in a culture fluid and need to be adhered to a Schale such as glass for proliferation. Therefore, when the cells are made to gather at the same place in polytetrafluoroethylene, the cells will adhere to each other seeking for anchorage, thereby resulting formation of a cellular aggregate, namely, a spheroid. Furthermore, when the spheroids adhere and fuse together, a larger shape will result.

Due to the intervention of the step of spheroids, the cells enter the stationary phase of the cell cycle, whereby production of a protein is considered to increase. Thus, according to the present invention, since the cells are induced to enter the stationary phase, they are preferably once made into spheroids and then formed into a predetermined shape.

The culture fluid used for cell cultivation may be a commonly used synthetic or natural medium depending on the cell to be cultured.

Considering infection with a bacterial virus or the like resulting from an animal-derived substance, supplying season and quality stability, a synthetic medium is favorable.

As a synthetic medium, for example, α-MEM (Minimum Essential Medium), DMEM (Dulbecco's Modified Eagle Medium), RPMI 1640 medium, CMRC medium, HAM medium, DME/F12 medium, MCDB medium or the like can be used.

These media may appropriately be added with a proliferative factor, a growth factor, a biologically active substance such as a hormone, or other various substances having pharmacological actions. Addition of such substances can give or change the function of the medium.

Examples of a growth factor or a cellular proliferative factor include bone morphogenetic protein (BMP), fibroblast growth factor (FGF), transforming growth factor-β (TGF-β), insulin-like growth factor (IGF), platelet derived growth factor (PDGF), vascular endothelial growth factor (VEGF), known serum components such as transferrin (concentration is adjusted appropriately), various vitamins and antibiotics such as streptomycin.

Examples of hormones include insulin, transferrin, dexamethasone, hydrocortisone, thyroxine, 3,3',5-triiodothyronine, 1-methyl-3-butylxanthine and progesterone.

Typically, examples of other biologically active substances include vitamins such as ascorbic acid (particularly, L-ascorbic acid), biotin, calcium pantothenate, ascorbic acid 2-phosphate and vitamin D, proteins such as serum albumin and transferrin, lipids, fatty acid sources, linoleic acid, cholesterol, pyruvic acid, DNA and RNA synthetic nucleoside, glucocorticoid, retinoic acid, β-glycerophosphate and monothioglycerol.

The cultivation temperature of the cells is typically 35-40° C. and preferably around 37° C. The cultivation period may appropriately be adjusted according to the size of a cell construct (cell plug) of interest. For example, in order to culture embryonic stem cells, it is generally well known to conduct the cultivation, for example, under the conditions at a temperature of 37° C. and a carbon dioxide concentration of 5%.

Spheroids derived from the embryonic stem cells can be formed under the above-described conditions.

Figure 2:
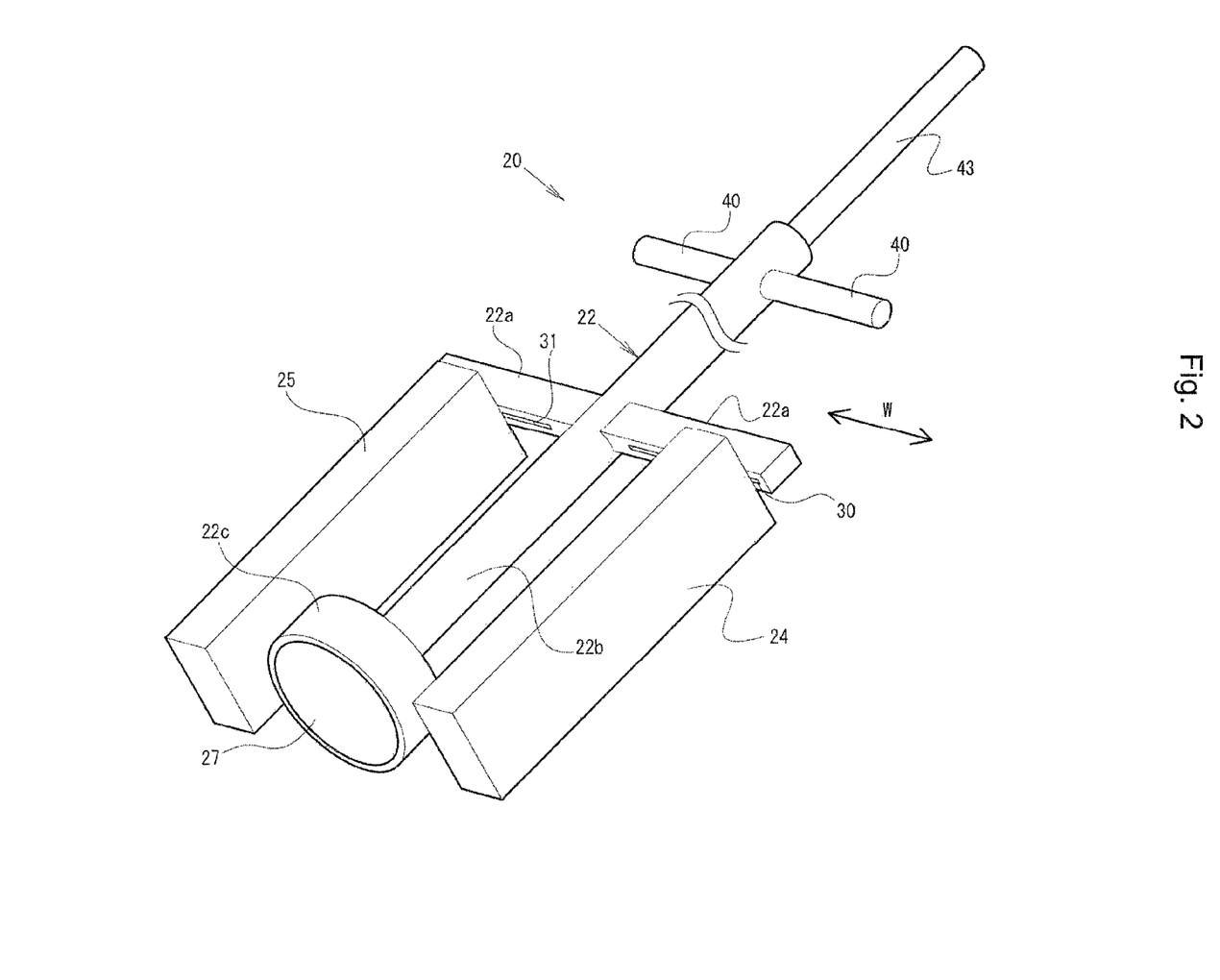
FIG. 2 A perspective view showing an appearance of a transplantation device which holds the open end side of the transplantation guide and retains a three-dimensional cell construct in the cylinder at a recipient site.

FIG. 2 is a perspective view showing an appearance of the transplantation device which holds an open end side of the transplantation guide and retains a three-dimensional cell construct in the cylinder at a recipient site. As can be appreciated from FIG. 2, the transplantation device 20 is provided with a main device body 22, sandwiching members 24 and 25, a retaining member 27, a holder 40, an operating rod 43 and the like. The main device body 22 has a slider 22a for holding the sandwiching members 24 and 25 arranged on both sides to allow them to slide in the W-direction, a guidance tube 22b that holds the retaining member 27 to be capable of being pushed out, and a receiver 22c for sandwiching the transplantation guide 2 with the opposing sandwiching members 24 and 25.

The slider 22a, for example, is provided with slide guides 30 and 31 for sliding the sandwiching members 24 and 25, and projections (not shown) that engage with these slide guides 30 and 31 are formed on the sandwiching members 24 and 25, respectively. A mechanism for slidably holding the sandwiching members 24 and 25 is not limited to the above-described mechanism and any appropriate mechanism may be used.

The shape and the material of the sandwiching members 24 and 25 may appropriately be determined according to the material of the transplantation guide 2 and the shape of the receiver 22c. For example, they may be formed with elastically deformable polyurethane that has a relatively high friction coefficient so as to fit the shape of the receiver 22c of the opposing main device body 22. By forming the sandwiching members 24 and 25 with such a material, the sandwiching members 24 and 25 get dented to fit the outer periphery of the receiver 22c of the main device body 22, by which the sandwiched area of the transplantation guide 2 increases which can be expected to result in stronger sandwiching of the transplantation guide 2.

The sandwiching members 24 and 25 slidably held by the slider 22a slides in the W-direction, by which, for example, the open end 4a side of the transplantation guide 2 can be sandwiched.

The inner periphery of the open end 4a of the cylindrical body 4 opposes the receiver 22c while the outer periphery of the open end 4a of the cylindrical body 4 opposes the sandwiching members 24 and 25. As a result, the open end 4a side of the cylindrical body 4 is sandwiched by being pressed against the receiver 22c by the sandwiching members 24 and 25. There are various mechanisms for engaging the sandwiching members 24 and 25 on the slider 22a and any method, for example, a method in which each of the sandwiching members 24 and 25 is engaged to the slider 22a with a screw or a method in which each of the sandwiching members 24 and 25 is engaged to the slider 22a with an engaging claw, may appropriately be selected.

Figure 3:
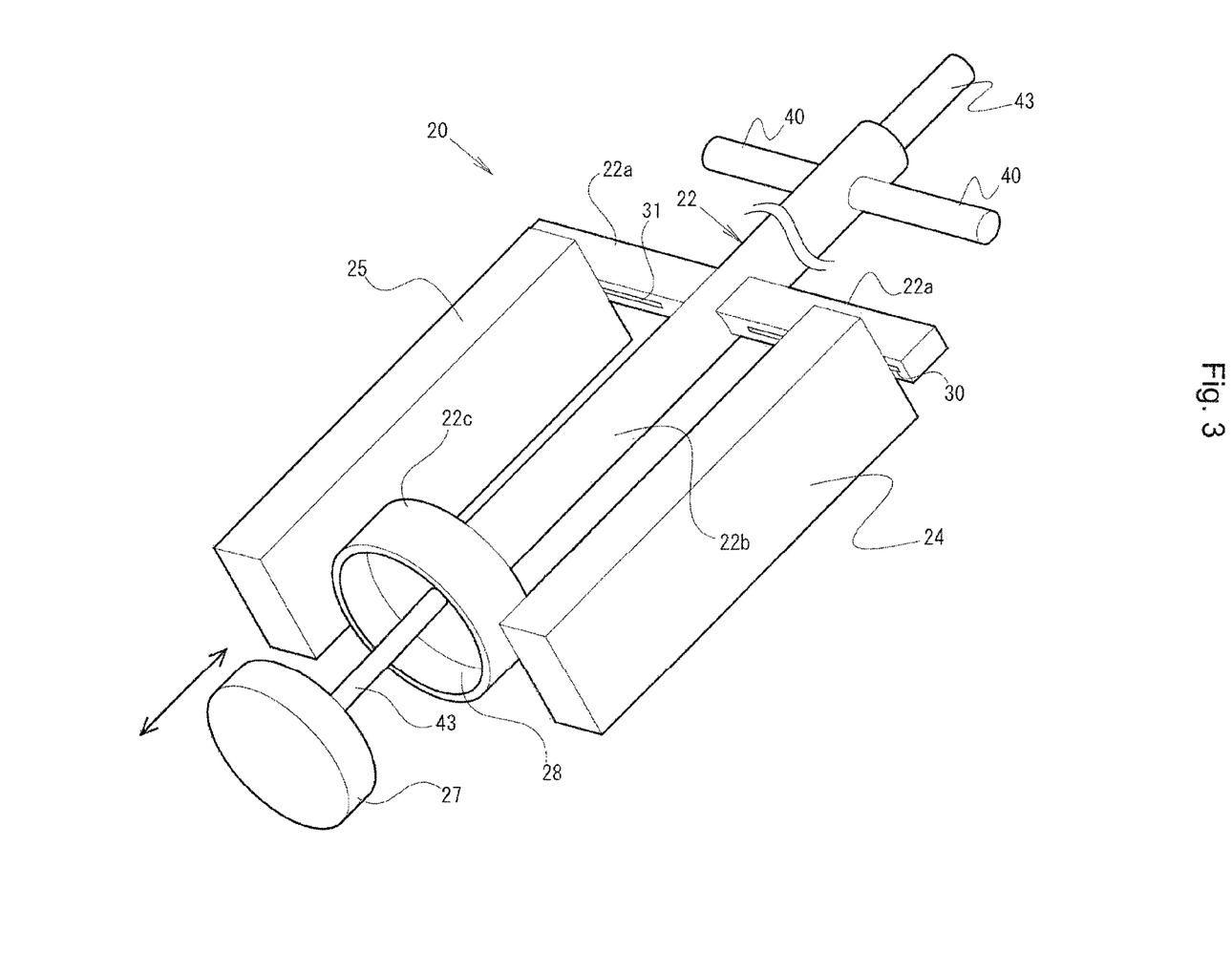
FIG. 3 A perspective view showing an appearance of the transplantation device where the retaining member is protruding from the guidance tube.

FIG. 3 is a perspective view showing an appearance of the transplantation device where the retaining member is protruding from the guidance tube. As shown in FIG. 3, the guidance tube 22b supports the retaining member 27 such that the retaining member 27 can protrude from the receiver 22c, by which the retaining member 27 can enter the transplantation guide 2 that is sandwiched between the receiver 22c and the sandwiching members 24 and 25. The guidance tube 22c is provided with a chamber 28 for receiving the retaining member 27, and the retaining member 27 is usually accommodated in this chamber 28.

The main device body 22 is provided with a holder 40 that is to be held by a user (including a robot whose movement is controlled by the commands from the user), and an operating rod 43 manipulated by the user. One end of the operating rod 43 is manipulated through pressing by the user while the other is provided with a retaining member 27. The main device body 22 may further be provided with an automatic return structure that automatically sends the retaining member 27 back into the chamber 28.

As one example of the automatic return structure (not shown), for example, the operating rod 43 is biased with a spring (not shown) that applies force from one side of the operating rod 43 having the retaining member 27 toward the other end that is to be manipulated through pressing by the user, in which case the operating rod 43 is pressed by the user against this biasing force. When the operating rod 43 is pressed by the user, the retaining member 27 protrudes from the receiver 22c. In this case, it is preferable that the user brings the retaining member 27 into contact with the three-dimensional construct without harming the three-dimensional construct. Once the retaining member 27 makes contact with the three-dimensional construct, the holder 40 can be pulled up to withdraw the cylindrical body 4 so that the three-dimensional construct is retained at the recipient site. When the user let go of the operating rod 43, the operating rod 43 returns to the original position due to the biasing force of the spring, by which the retaining member 27 is accommodated in the chamber 28 and returns back to its initial position.

Figure 4:
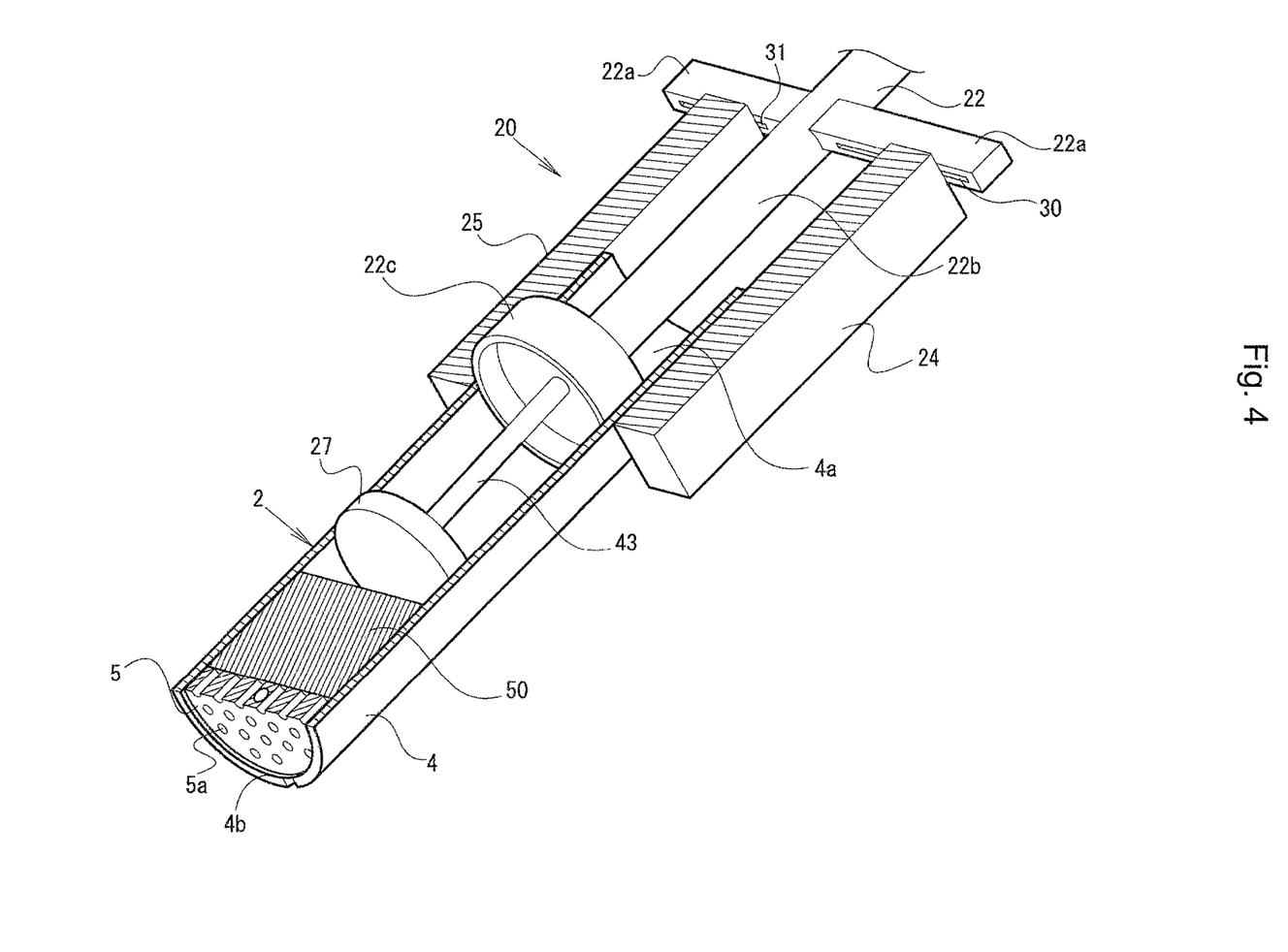
FIG. 4 A cross-sectional perspective view of the transplantation device and the transplantation guide held by this transplantation device, partially cutting along a plane extending from the base material side toward the open end side of the transplantation guide.

FIG. 4 is a cross-sectional perspective view of the transplantation device and the transplantation guide held by this transplantation device, partially cutting along a plane extending from the base material side toward the open end side of the transplantation guide. As shown in FIG. 4, the receiver 22c makes contact with the inner periphery of the open end 4a of the transplantation guide 2 while the sandwiching members 24 and 25 make contact with the outer periphery thereof. Accordingly, the transplantation guide 2 is held by the transplantation device 20, thereby providing a three-dimensional construct 50 in the transplantation guide 2.

The three-dimensional construct 50 is formed, for example, into a column on a base material 5. The retaining member 27 makes contact with this three-dimensional construct 50 and makes the three-dimensional construct, together with the base material 5, to retain at the recipient site. The base material 5 is provided to be movable inside the cylindrical body 4 so that it slides inside the cylindrical body 4 together with the three-dimensional construct 50 making contact with the retaining member 27. Once the opening 4b of the cylindrical body 4 is inserted into the recipient site, the cylindrical body 4 is pulled up from the recipient site while leaving the retaining member 27 to make contact with the three-dimensional construct 50 so that the base material and the three-dimensional construct are left at the recipient site.

Hereinafter, a method and an embodiment for delivering the base material 5 and the three-dimensional construct 50 to the recipient site in a more certain way will be described.

The components exemplified below are not essential but preferably provided in order to deliver the three-dimensional construct 50 to the recipient site in a stable and more certain way.

Figure 5:
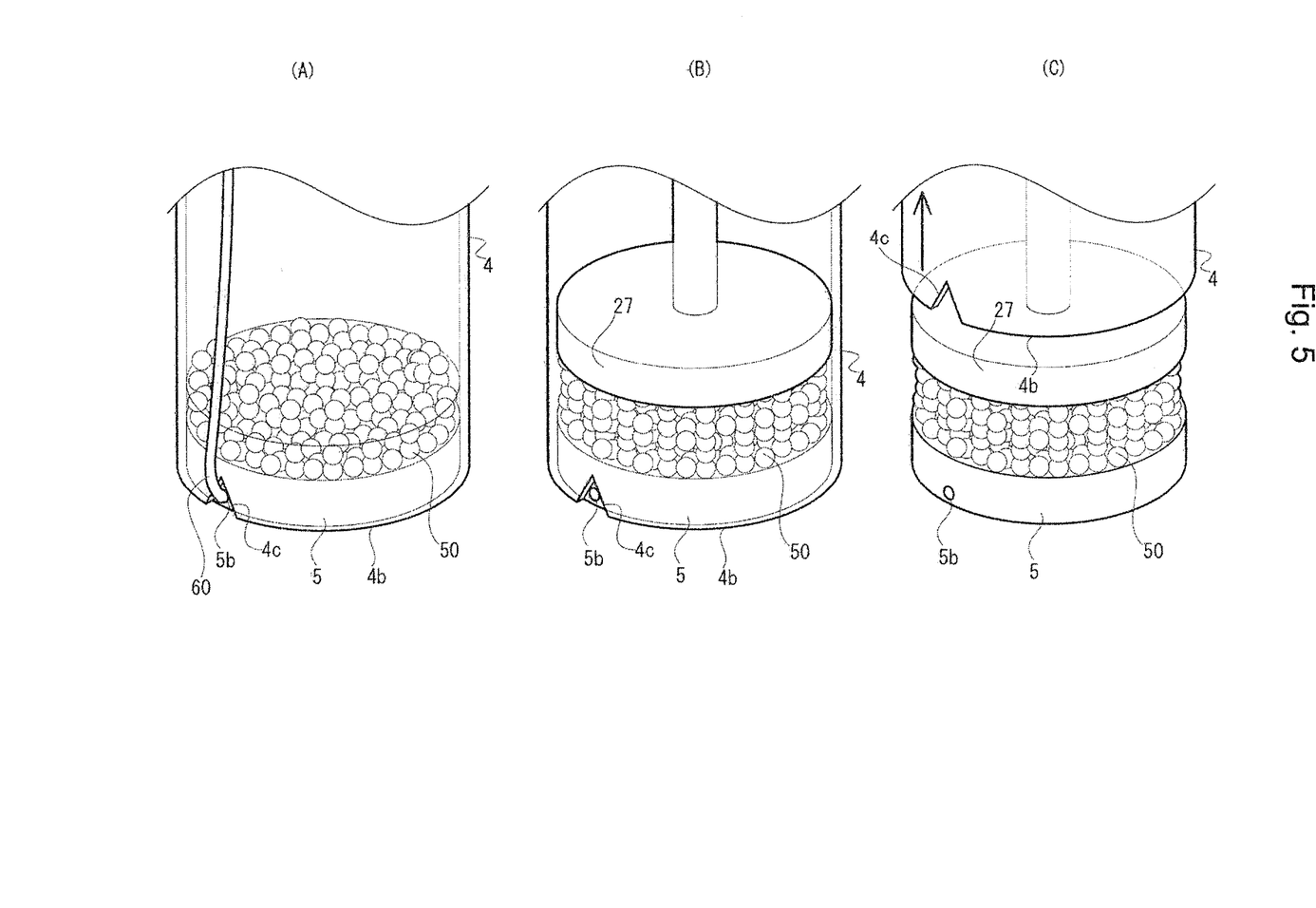
FIG. 5 A view exemplifying one embodiment of an end of a transplantation guide that is inserted into a recipient site and illustrating a workflow of transplanting a three-dimensional cell construct into the recipient site.

FIG. 5 is a view exemplifying one embodiment of an end of transplantation guide that is inserted into a recipient site and for illustrating a workflow of transplanting a three-dimensional cell construct into the recipient site. The end 4b of the transplantation guide 4 that is to be inserted into the recipient site is provided, for example, with a generally V-shaped notch 4c. The base material 5 is provided with an throughhole 5b into which a liner member for stably introducing the base material 5 into the recipient site is inserted. A notch 4c is formed in the transplantation guide 4 and the base material is provided with the throughhole 5b into which the linear member 60 is inserted in advance so that the three-dimensional construct can be introduced into the recipient site in a more certain way. Examples of the linear member 60 include threads made of cotton, silk, polymers such as polyester or metals such as stainless.

As shown in FIG. 5(A), the linear member 60 that has been passed through the throughhole 5b of the base material 5 having the three-dimensional construct 50 engages with the notches 4c formed in pairs at the end of the transplantation guide 4. The number of notches may correspond to the number of the throughhole 5b and may be, for example, two, four, six or the like. Herein, a case will be described where one throughhole 5b is formed in the base material 5 and two notches 4c, corresponding to this one throughhole 5b, are formed at the end of the transplantation guide 4.

Once the retaining member 27 is brought into contact with the three-dimensional construct 50, the linear member 60 hooked through the notch 4c is held tight while the end of the transplantation guide 4 is inserted into the recipient site. Since the linear member 60 is held tight, the base material 5 is stably held at the end of the transplantation guide 4, and the base material 5 and the three-dimensional construct 50 are inserted into the recipient site. Once the base material 5 and the three-dimensional construct 50 are introduced into the recipient site, the linear member 60 is pulled out from the throughhole 5b, where the base material 5 becomes freely slidable in the transplantation guide 4 (see FIG. 5(B)). By pulling out the transplantation guide 4 from the recipient site leaving the retaining member 27 to make contact with the upper part of the three-dimensional construct 50, the base material 5 and the three-dimensional construct 50 are retained at the recipient site (see FIG. 5(C)).

Next, operation of the present invention will be described. Cell masses are placed inside the cylindrical transplantation guide 2, and the base material 5 side of the transplantation guide 2 is immersed in the vessel 7 accommodating an excessive amount of a culture fluid. The base material 5 side of the transplantation guide 2 allows communication of the culture fluids inside and outside the transplantation guide 2. The cell masses such as spheroids are further and three-dimensionally cultured with this culture fluid. The cylindrical body 4 is formed, for example, with polytetrafluoroethylene (PTFE) so that the look of the three-dimensional construct 50 can be observed from outside. Cultivation of the spheroids results in formation of a three-dimensional construct 50, which is formed, for example, into a column following the inner shape of the cylindrical body 4. Accordingly, the transplantation guide 2 serves as a mold (template) upon formation of the three-dimensional construct 50.

After the three-dimensional construct 50 is formed, the open end 4a of the transplantation guide 2 is sandwiched between the sandwiching members 24 and 25 and the receiver 22c of the transplantation device 20. The opening 4b at the base material 5 side of the transplantation guide 2 sandwiched by the transplantation device 20 is inserted into the affected area, where the three-dimensional construct 50 is supplied from the transplantation guide 2 to the recipient site of a patient by the user.

A procedure for this operation by the user, for example, include inserting the receiver 22c of the transplantation device 20 into the open end 4a of the transplantation guide 2, and sliding the sandwiching members 24 and 25 toward the receiver 22c from both sides to sandwich the open end 4a of the transplantation guide 2.

Once the open end 4a is sandwiched, the user inserts the opening 4b of the transplantation guide 2 into the recipient site. In the case of a structure in which the linear member 60 passed through the throughhole 5b of the base material 5 is engaged with the notch 4c of the cylindrical body 4 to hold the base material 5 as shown in FIG. 5, the transplantation guide 2 is inserted into the recipient site while holding the linear member 60 tight so that the base material 5 and the three-dimensional construct 50 can surely and stably be delivered to the recipient site. Once delivery of the base material 5 and the three-dimensional construct 50 is confirmed, the linear member 60 is withdrawn so that the base material 5 becomes free to slide in the cylindrical body 4.

After the opening 4b of the cylindrical body 4 is inserted into the recipient site, the user presses the operating rod 43 so as to bring the retaining member 27 into contact with the three-dimensional construct 50. At this point, the user needs to be careful not to harm the three-dimensional construct 50 with the retaining member 27.

After bringing the retaining member 27 into contact with the three-dimensional construct 50, the user pulls up the holder 40 while the three-dimensional construct 50 is held at the recipient site with the retaining member 27 (see FIG. 3) so that only the cylindrical body 4 can be withdrawn from the recipient site, leaving the base material 5 and the three-dimensional construct 50 to be retained at the recipient site. Since the base material 5 is made of a biodegradable material, it will disappear in due time and only the three-dimensional construct 50 will remain at the recipient site to treat the affected area. After culturing and forming the three-dimensional construct 50, the base material 5 may be removed with a surgical knife immediately before inserting the three-dimensional construct 50 into the affected area, but by forming it with a biodegradable material, the user can easily perform the transplantation of the three-dimensional construct 50, thereby further enhancing convenience.

The cylindrical body 4 is formed to have a thickness of, for example, 0.1 mm, by which a three-dimensional construct 50 with a size closer to the size of the recipient site can be supplied to the recipient site. Accordingly, a higher therapeutic effect can be expected. In addition, the thinner the transplantation guide 2 is, the closer the size of the three-dimensional construct supplied to the affected area will be to the size of the affected area, and thus higher therapeutic effect can be expected. Therefore, the cylindrical body 4 is made of a strong material that is as thin as possible.

Thus, since the transplantation guide of the present invention serves as a mold for forming a three-dimensional construct and also serves as a guide for supplying the three-dimensional cell construct to a recipient site, the number of user's tasks for cultivation and transplantation can be reduced, thereby enhancing convenience.

In addition, the transplantation device of the present invention allows the transplantation guide inserted into the recipient site to be withdrawn from the recipient site while leaving the three-dimensional cell construct to be retained at the recipient site.

In the aforementioned description, the transplantation device 20 is used to deliver the three-dimensional construct in the transplantation guide 2 to an affected area. In the case where the transplantation guide 2 is formed with a relatively rigid material such as stainless, however, the user can directly grasp the outer periphery of the cylindrical body of the transplantation guide, and the three-dimensional construct in the transplantation guide can be retained at the recipient site through manual manipulation.

REFERENCE NUMERALS

2 Transplantation guide
4 Cylindrical body
4a Open end
4b Opening at base material side
4c Notch
5 Base material
5a Micropore
5b Throughhole
7 Vessel
10 Culture fluid
20 Transplantation device
22 Main device body
22a Slider
22b Guidance tube
22c Sandwiching receiver
24 Sandwiching member
25 Sandwiching member
27 Retaining member
30 Guide slot
31 Guide slot
40 Holder
43 Operating rod
50 Three-dimensional construct
60 Linear member

The invention claimed is:

1. A method for transplantation of a three-dimensional cell construct into a recipient site of a patient, said method comprising the steps of:
   providing a transplantation guide in the form of an open cylinder having a top and a bottom and being formed from a transparent or semi-transparent material, wherein a disk of biodegradable material that allows passage of a culture fluid is held within the bottom of said transplantation guide and has an inner diameter of the bottom of the transplantation guide, and wherein the external thickness of the entire cylinder is 0.05-0.3 millimeters;
   placing a cell mass supplied from the top side onto said disk;
   subjecting said cell mass located on the top side of said disk to immersion in an excessive amount of a culture fluid and culturing said cell mass, thereby forming a three-dimensional cell construct, wherein the disk together with the three-dimensional cell construct is configured to transfer from the bottom of the cylinder and to be retained at a recipient site;
   providing a transplantation device comprising a main device body, sandwiching members oppositely arranged on sides of the main device body, an operating rod, and a retaining member provided at an end of the operating rod, wherein the main device body of the transplantation device has a slider, a guidance tube, and a receiver at an end of the guidance tube, the slider is configured to hold the sandwiching members to allow them to slide in a direction perpendicular to a longitudinal direction of the guidance tube, the guidance tube is configured to movably hold the operating rod within the guidance tube, the receiver has a chamber that accommodates the retaining member, and the receiver is configured to sandwich the transplantation guide with the sandwiching members;

sandwiching the transplantation guide with the sandwiching members and the receiver;

bringing the retaining member into contact with the three-dimensional cell construct;

inserting the bottom of the transplantation guide into the recipient site of the patient;

inserting the three-dimensional cell construct formed on the top side of said disk into the recipient site of the patient; and withdrawing the transplantation guide from the recipient site while leaving the three-dimensional cell construct placed on the disk retained at the recipient site of the patient, wherein notches are formed in pairs at the bottom end of the transplantation guide; a throughhole into which a linear member is inserted in advance formed at the disk and a linear member that has been passed through the throughhole of the disk is engaged with the notches, and wherein the step of inserting the bottom of the transplantation guide comprises: tightly holding the linear member hooked through the notches while the bottom of the transplantation guide is inserted into the recipient site of the patient arid pulling out the linear member from the throughhole so that the disk becomes freely slidable in the transplantation guide.

2. The method of claim 1, wherein said cylinder is composed of a material selected from the group consisting of polytetrafluoroethylene, polychlorotrifluoroethylene, polyvinylidene difluoride, polyvinyl fluoride, and polytetrafluoroethylene-hexafluoropropylene copolymer.

3. The method of claim 1, wherein said disk of biodegradable material comprises pores having diameters in the range 10-500 µm.

4. The method of claim 1, wherein said disk of biodegradable material is composed of a material selected from the group consisting of alpha-tricalcium phosphate, beta-tricalcium phosphate, and hydroxyapatite.

5. The method of claim 1, wherein said cell mass comprises cellular spheroids.

6. The method of claim 1, wherein said recipient site is selected from the group consisting of bone, cartilage, ligament, and adipose tissue.

* * * * *